United States Patent [19]
Usala

[11] Patent Number: 5,908,633
[45] Date of Patent: Jun. 1, 1999

[54] BIOARTIFICIAL HORMONE RELEASING DEVICE

[76] Inventor: Anton-Lewis Usala, 237 Buckingham Dr., Winterville, N.C. 27890

[21] Appl. No.: 08/787,316

[22] Filed: Jan. 24, 1997

Related U.S. Application Data

[63] Continuation of application No. 08/346,340, Nov. 28, 1994, Pat. No. 5,614,205, which is a continuation of application No. 07/841,973, Feb. 24, 1992, abandoned.

[51] Int. Cl.$^6$ .............................. A61F 2/02; A61K 47/30
[52] U.S. Cl. ........................................ 424/424; 514/772.3
[58] Field of Search ........................... 424/424; 514/772.3

[56] References Cited

U.S. PATENT DOCUMENTS 5,614,205   3/1997   Usala ...................................... 424/424

*Primary Examiner*—Carlos A. Azpuru
*Attorney, Agent, or Firm*—Bell Seltzer Intellectual Property Law Group of Alston & Bird LLP

[57] ABSTRACT

A device for the effective release of hormones wherein a matrix containing a hormone producing cellular moiety is encapsulated with a non-immunogenic polymeric material of poly-para-xylyene having a membrane portion with a porosity blocking passage therethrough of immunogenic agents and permitting passage therethrough of effective nutrients for said cellular moiety and the hormone produced thereby.

15 Claims, 1 Drawing Sheet

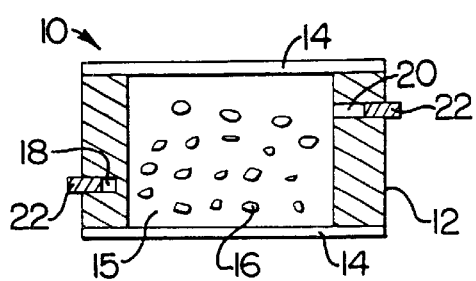
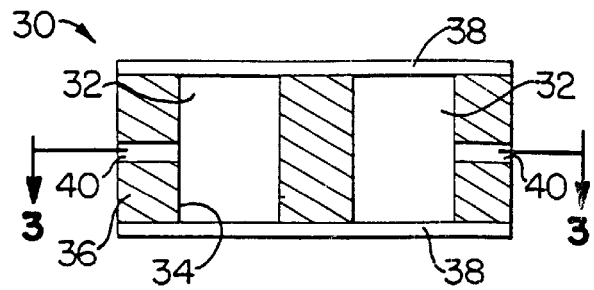
FIG. 1.  FIG. 2.
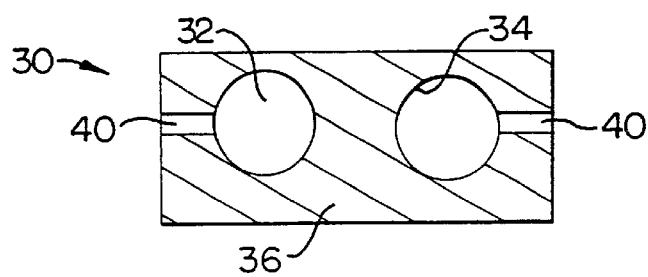
FIG. 3.
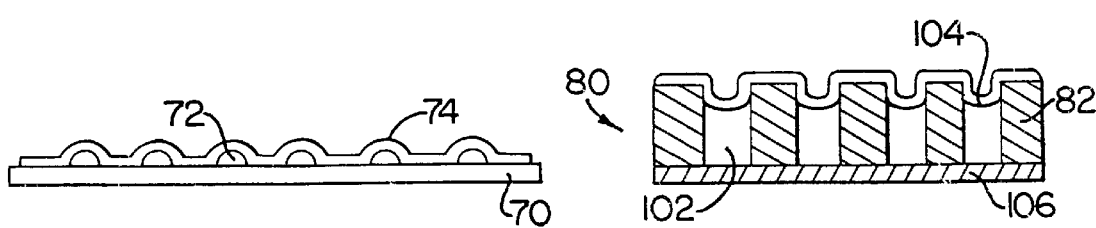
FIG. 4.  FIG. 5.

BIOARTIFICIAL HORMONE RELEASING DEVICE

This application is a continuation of application Ser. No. 08/346,340, filed Nov. 28, 1994, now U.S. Pat. No. 5,614, 205, which is a File Wrapper Continuation application of Ser. No. 07/841,973, filed Feb. 24, 1992, now abandoned.

BACKGROUND OF THE INVENTION

The present invention relates to the encapsulation of hormone producing tissue, and, in particular, to the membrane encapsulation of insulin producing pancreatic islets for xenographic transplantation into diabetic subjects.

Diabetes Mellitus is an affliction affecting approximately 20 million persons in the United States of America alone. This affliction is characterized by either a near total lack of insulin (Type I diabetes) or a resistance to normal levels of circulating insulin (Type II diabetes). Both conditions can currently be controlled to some extent by daily subcutaneous injections of exogenous insulin. Because the insulin injections are periodically spaced in predetermined doses, the regimen functions as an open loop system, not releasing insulin in accordance with metabolic demand and thereby regulating blood glucose levels within ranges achieved by normal non-diabetic subjects. Accordingly, it is well recognized that this type of therapy has failed to achieve the necessary metabolic control of blood sugar to prevent the vascular complications associated with the disease. These complications include blindness, kidney failure, heart disease, stroke, and loss of peripheral sensory nerve function. Diabetes currently is the third largest disease cause of death in the United States, costing approximately $2–3 billion a year for treatment.

Insulin dispensing pumps, programmed or manually operated, for delivering insulin to the diabetic subject have been used to provide more numerous, smaller doses of insulin in an attempt to regulate blood glucose within narrower ranges. Such pumps, nonetheless still function as an open loop system, only attempting to anticipate, but not respond to metabolic demand. The therapeutic efficacy of current pumps over conventional insulin injection is not clearly established or clinically accepted. There have been attempts to regulate pumps with blood glucose sensors to provide closed loop control, but to date an implantable sensor with long term biocompatibilty and functionality has not been achieved.

Medical researchers for many years have recognized the desirability of closed loop implantable devices incorporating live insulin producing tissue, islets or isolated beta cells, which release through a selective, permeable membrane, in accordance with metabolic demand. These devices, termed "bioartificial pancreases" have been medically defined in terms of functional and performance constraints. First, the tissue must respond and release insulin in required amounts within an appropriate time to increases and decreases in blood glucose concentration. Second, the device must support and not suppress insulin production. Third, the device must provide protection against immune rejection. Fourth, the islets must survive functionally or the device easily replaced. Fifth, the membrane must be appropriately selective and biocompatible with the patient and its functional properties not altered by contact with host tissue.

Various capsule approaches have been taken with regard to physical devices containing islets, using planar or tubular membranes. Generally, these have failed due to lack of biocapatiblity leading to fouling of the membrane. In attempts to overcome rejection, highly purified beta cells have been implanted into human subjects taking large doses of effective immunosuppressents such as cyclosporin. As far as known, there have not been any successful implantations using this approach.

Recently, islets have been macroencapsulated in a hydrogel such as sodium alginate and injected into hollow fibers formed by a dry-wet spinning technique using an acrylic copolymer. While demonstrating an ability to control glucose levels in mice, the long term biocompatibility of the fibers has not been established.

BRIEF SUMMARY OF THE INVENTION

The present provides an implantable device satisfying the above criteria while overcoming the aforementioned problems to provide closed loop insulin delivery in accordance with demand and overcoming the the above problems of rejection by selectively protecting the pancreatic islets from the host's immune defenses by a recognized biocompatible material. More particularly, the islets, human or preferably animal which are more readily available, in either cellular form or within enclosure devices, are encased with a polymeric material comprising poly-para-xylylene having a membrane portion with a porosity permitting passage of nutrients, glucose signals, electolytes, water, and the egress of insulin released by the islets, all of which have a molecular weight of less than about 5,000. The porosity of the membrane, however, is less than immunoglobulins, having molecular weights of 160,000–500,000. Poly-para-xylylene in particular is recognized as a biocompatible surface substrate for implantation and does not interact with plasma factors such as fibrin or cells such as platelets. Accordingly, the capsule pores will not become clogged, and insulin release as a function of the host's own glucose concentration will be effected. The device may take various designs based on fresh or frozen islets and configured in various cell arrays, while providing the selective membrane porosity of the poly-para-xylylene a biocompatibility for the interior and exterior surfaces thereof.

BRIEF DESCRIPTION OF THE DRAWINGS

The above and other features and advantages of the present invention will become apparent upon reading the following written description of the preferred embodiments, taken in conjunction with the accompanying drawings in which:

FIG. 1 is a side cross sectional view of bioartificial endocrine device in accordance with an embodiment of the present invention;

FIG. 2 is a side cross sectional view of another embodiment of the present invention;

FIG. 3 is a cross sectional view taken along line 3—3 in FIG. 2;

FIG. 4 is a side cross sectional view of another embodiment of the present invention; and FIG. 5 is a cross sectional view of a further embodiment of the invention;

DESCRIPTION OF THE PREFERRED EMBODIMENTS

Referring to the drawings for purposes of describing the preferred embodiments only, FIG. 1 shows a bioartificial endocrine device 10 for the effective release of hormones. The device 10 comprises a circular cylinder 12 having a pair of selective permeable membranes 14 attached by a biocompatible adhesive to the top and bottom end faces thereof. A suitable adhesive for attachment of the membrane to the sleeves and the sleeves to each other are silicone adhesives, Silastic Type A manufactured by Dow-Corning, cyanoacrylates, Prism 454 manufactured by Locktite Corporation, epoxies or other adhesives, preferably biocompatible, providing sufficient adhesion to sealingly maintain the integrity of the cavity. The interior volume of chamber 15 is defined by the inner wall of the cylinder 12 and the membranes 14. The chamber 15 contains hormone producing tissue, preferably porcine pancreatic islets, or other hormone producing cellular moieties 16 in a liquid or gel matrix. Prior to filling, the assembled device is heat or radiation sterilized. The side wall of the cylinder 12 is provided with a lower radial port 18 for introducing the cellular matrix into the chamber 15 and an upper radial port 20 for venting the chamber 15 during filling. The ports 18, 20 are sealed by sterile biocompatible sealing members 22.

The cylinder 12 may be formed of any suitable material, such as metal or plastic. The membranes 14 are polymeric films of poly-para-xylylene (poly-para-xylylene N), or analogs thereof such as poly-monochloro-xylylene (poly-para-xylylene C), and poly-dichloro-xylylene (poly-para-xylylene D). The membranes 14 have a porosity which blocks passage therethrough of immunogenic agents while permitting passage therethrough of effective nutrients for the cellular moiety and the hormone produced thereby. For a bioartificial pancreatic device, as described below, membranes comprising poly-para-xylylene N at a thickness of about 2500 to 5000 Angstroms, and preferably about 2500 to 3500 Angstroms, provide the desired porosity characteristics.

The membranes are formed by conventional vacuum deposition and have a porosity which can accurately be controlled such that a selective membrane may be established at a thickness less than about 1000 Angstroms. In the present embodiment, the maximum pore size is selected to prevent the passage of immunoglobulins and antibodies having molecular weights of 40,000 to about 500,000. The minimum pore size is selected to permit the passage of nutrient molecules, such as glucose, electrolytes and water, and the hormone, insulin having a molecular weight of around 5,600.

EXAMPLE 1

A membrane of poly-para-xylylene N having a thickness of 3,271 Angstroms was mounted on a cylindrical sleeve and partially immersed in distilled water. A liquid containing components of varying molecular weights was placed on the upper surface of the membrane. Thereafter samples of the water were applied to an SDS-PAGE gel and subjected to electrophoresis to separate the samples according to molecular weights. Low molecular weights corresponding to glucose, insulin and cell nutrients were identified. Higher molecular weight components, i.e. greater than 26,000, were excluded.

More particularly, for an implantable bioartificial pancreatic device, the cellular moiety contains a plurality of insulin producing islets. The islets are derived from donor pancreatic organs, both human and animal, in conventional manner utilizing collagenous digestion and Ficoll gradient separation. The islets are admixed with conventional RPMI culture media to form the matrix at a concentration of around 10 to 50 islets per microliter.

The cylinder chamber may vary in size and shape for purpose of handling, coating and implantation considerations as well as the therapeutic insulin production required by the recipient.

For purposes of implant biocompatibility, the cylinder may be formed of a suitable material such as medical grade stainless steel or preferably by conformal coating with poly-para-xylylene, the thickness or which is not particularly critical, however a coating thickness of about 0.5 microns is preferred. This coating may be precisely applied in controlled thicknesses according to conventional techniques. The coating and membrane materials are recognized as non-immunogenic substrates for human implantation. The material does not interact with plasma factors such as fibrin or cells such as fibroblasts or platelets. Accordingly, the device and membrane pores will not become clogged or impair insulin release as a function of the host tissue growth.

EXAMPLE 2

A membrane of poly-para-xylylene N at a thickness of around 3100 Angstroms was mounted on a cylindrical sleeve and partially immersed in a media, distilled water. Seventy-five (75) adult porcine islets were placed in RPMI culture media on the top surface of the membrane. The media was periodically sampled and changed after sampling. Two aliquots were extracted from the media on the fourth and sixth days. The aliquots were tested in duplicate in an $I^{125}$ Insulin RIA (Ventrex). Insulin levels on the sample from the fourth day was 70+149 uU/ml and on the sample from the sixth day was 235+150 uU/ml., demonstrating that insulin secreted from the islets traversed the membrane. No fibrin or lymphaction attachment occurred.

EXAMPLE 3

An implant device was prepared using two PVC sleeves, ½" O.D., ⅜" I.D., 3/16" thickness. The sleeves were coated with poly-para-xylylene N to a thickness of about 0.5 microns. Circular poly-para-xylylene membranes having a thickness of 2950 Angstroms were adhered to the top surfaces of the sleeves with silicone adhesive. The sleeves were then radiation sterilized.

One membrane sleeve was filled with 20 deciliter of cellular matrix. The matrix included porcine beta cell islets numbering about 5,000. The islets were prepared in accordance with the colloganese digestion method. Thereafter the sleeves were joined with a silicone adhesive. The device was implanted into the peritoneal cavity of a non-obese diabetic mouse.

For three weeks prior to implant, the fasting blood glucose (FBG) of the mouse was 760 mg/dl as determined by glucose oxidase analysis. On the day following implantation, the fasting blood glucose level was 380 mg/dl. When the device was removed following implant, no fibroid or lymphoblastic attachment to the device or the membrane was observed.

EXAMPLE 4

An implant device was constructed in accordance with the embodiment of FIG. 1. The collar had an outside diameter of ½ inch and an inner diameter of ¼ in. A membrane of around 3000 A poly-para-xylylene N was adhered to the faces of the collar with a silicone adhesive. Through radial fill holes the interior volume of the device was filled with approximately 5,000 adult porcine islets. The fill hole was sealed with a silicone plug. Four such devices were implanted into the peritoneal cavity of a pancreatized female mongrel dog weighing about 12 kg. Prior to the implant the dog without endogenous insulin administration during the preceding 24 hours did not indicate any plasma insulin. On the first day following implant, the plasma insulin levels were measured at 21.2 and 22.2 uU/ml. On the second day following implant, the plasma insulin levels were measured at 21.5 and 20.5 uU/ml.

Referring to FIGS. 2 and 3, a device 30 is provided with a plurality of cylindrical chambers 32 as defined by an array of through holes 34 in a generally rectangular poly-para-xylylene coated plate 36. The top and bottom of the holes 32 are sealed by poly-para-xylylene membranes 38 as described above. Cellular tissue in a liquid matrix is delivered to the chambers 32 through radial fill ports 40 which are thereafter sealed by plugs. The array of chambers 34 provides redundancy for the device 30 in the event of membrane breakage or fouling, decrease in cellular output and the like.

Referring to FIG. 4, a device comprises a plate 70 having a plurality of cellular droplets 72 arrayed thereon and covered with a membrane 74 of poly-para-xylylene as described above. The device is formed by depositing the tissue media in liquid form or macroencapsulated in a protective covering, such as sodium alginate, on a poly-para-xylylene coated plate. After deposition, the droplets and plate coated to the desired thickness with poly-para-xylylene. Alternatively, the droplets and plate are frozen, coated, and, when ready for implant, the device is thawed to reconstitute the cells. The cells may be frozen and thawed according to the protocol set forth R. V. Rajotte (Cryopreservation of Isolated Islets, 2nd International Conference on Use of Human Tissues and Organs Search In Transplant, Oct. 1985, pages 46–51).

The devices may be formed as individual droplets which are encapsulated with the aforementioned membrane. The individual droplets, frozen or as macrocapsules, may be conventionally coated in a free fall coating process or suspended from an embedded thread and coated. The cells are thereafter reconstituted, admixed in an appropriate media and may then be implanted by injection into the selected site.

The device 80 may also take the form shown in FIG. 5. More particularly, a rectangular plate 82 is provided with a plurality of through holes 102. The top surface of the plate and the top openings of the holes being coated with poly-para-xylylene coating 104, and establishing the aforementioned membrane. The bottom surface of the plate, and bottom openings of the holes are covered by a poly-para-xylylene coated backing cover 106 which is adhered thereto by a suitable biocompatible adhesive. The interior chambers defined by the side walls of the hole, the membrane and the cover are filled with insulin producing cells within a liquid or gel matrix.

The device is preferably manufactured by initially coating the plate with poly-para-xylylene so as to provide a continuous conformal coating on all surfaces including the walls defining the openings. The bottom wall is sealed and the holes filled with distilled water to a level slightly below the top surface. The filled plate is then frozen, and thereafter coated with poly-para-xylylene to the desired membrane thickness. After coating, the device is warmed to thaw, the backing plate removed and the water removed through evaporation. The device is inverted and the desired cellular concentration deposited in the holes onto the membrane. The backing plate is then adhered as mentioned to the bottom surface.

Alternatively, cellular containing media may be frozen within the holes and the plate conformally coated to membrane thickness, and the cells unthawed as described above. In such a device, top and bottom membranes would be provided at each compartment.

The aforementioned encapsulation may be effectively utilized in other applications for hormone producing or tissue producing implantation into deficient individuals with conditions such as thyroid deficiency, growth hormone deficiency, congenital adrenal hyperplasia and the like.

Various modifications of the above described embodiments will be apparent to those skilled in the art. Accordingly, the scope of the invention is defined only by the accompanying claims.

What is claimed:

1. A bioartificial device for releasing a hormone in a recipient patient, comprising: a matrix containing a hormone producing cellular moiety; and capsule means enveloping said matrix comprising a polymeric membrane selected from the group consisting of poly-para-xylylene, poly-monochloro-xylylene, and poly-dichloro-xylylene, said polymeric membrane having a molecular weight porosity at least as great as that necessary to permit passage of therethrough of nutrient for said cellular moiety and the hormone produced thereby, but less than that necessary to block passage therethrough of immunogenic agents.

2. A bioartificial device of claim 1 wherein said polymeric membrane has a molecular weight porosity of less than 160,000.

3. A bioartificial device of claim 1 wherein said polymeric membrane has a molecular weight porosity of less than 40,000.

4. A bioartificial device of claim 1 wherein said polymeric membrane is poly-para-xylylene.

5. A bioartificial device of claim 1 wherein said cellular moiety produces a thyroid hormone.

6. A bioartificial device of claim 1 wherein said polymeric membrane has a molecular weight porosity of a growth hormone.

7. A bioartificial device of claim 1 wherein said polymeric membrane has a porosity of an adrenal hormone.

8. A bioartificial device as recited in claim 1 wherein said polymeric membrane has a thickness of around 2,000 to 5,000 Angstroms.

9. A bioartificial device as recited in claim 1 wherein said matrix comprises a liquid.

10. A bioartificial device as recited in claim 1 wherein said matrix comprises a gel.

11. A bioartificial device as recited in claim 1 wherein said matrix comprises culture media.

12. A bioartificial device as recited in claim 1 wherein said polymeric membrane has a thickness less than 5,000 Angstroms.

13. A bioartificial device as recited in claim 1 wherein said membrane has a thickness of around 2,500 to 3,500 Angstroms.

14. A bioartificial device comprising: capsule means for containing insulin producing cells formed of a biocompatible material including a permeable membrane formed of poly-para-xylylene, said membrane having a thickness less than about 5,000 Angstroms and permitting the passage therethrough of insulin.

15. A bioartificial device as recited in claim 14 wherein said capsule means comprises a plurality of chambers having openings covered by said permeable membrane.

* * * * *